US000001377H

United States Statutory Invention Registration [19]

[11] Reg. Number: H1377

Perry

[43] Published: Nov. 1, 1994

[54] ABSORBENT ARTICLE WITH MULTI-FUNCTIONAL TOPSHEET

[76] Inventor: Bruce F. Perry, 2625 Briarcliff Ave., Cincinnati, Ohio 45212

[21] Appl. No.: 23,023

[22] Filed: Feb. 25, 1993

[51] Int. Cl.[5] ..... A61F 13/15
[52] U.S. Cl. ..... 604/385.1; 604/378
[58] Field of Search ..... 604/385.1, 378, 369, 604/358

[56] References Cited

U.S. PATENT DOCUMENTS

| | | | |
|---|---|---|---|
| 3,929,135 | 12/1975 | Thompson | 128/287 |
| 4,324,246 | 4/1982 | Mullane et al. | 128/287 |
| 4,327,730 | 5/1982 | Sorensen | 128/287 |
| 4,342,314 | 8/1982 | Radel et al. | 128/287 |
| 4,395,215 | 7/1983 | Bishop | 425/290 |
| 4,463,045 | 7/1984 | Ahr et al. | 428/131 |
| 4,591,523 | 5/1986 | Thompson | 604/358 X |
| 4,609,518 | 9/1986 | Curro et al. | 264/504 |
| 4,629,643 | 12/1986 | Curro et al. | 604/385.1 X |
| 4,637,819 | 1/1987 | Ouellette et al. | 604/369 |
| 4,681,793 | 7/1987 | Linman et al. | 604/385.1 X |
| 4,772,444 | 9/1988 | Curro et al. | 604/385.1 X |
| 4,778,644 | 10/1988 | Curro et al. | 604/358 X |
| 4,846,813 | 7/1989 | Raley | 604/378 X |
| 4,846,821 | 7/1989 | Lyons et al. | 604/369 |
| 4,917,695 | 4/1990 | Villez | 604/385 X |
| 4,950,264 | 8/1990 | Osborn, III | 604/385.1 |
| 5,009,653 | 4/1991 | Osborn, III | 604/385.1 |
| 5,134,007 | 7/1992 | Reising et al. | 604/378 X |
| 5,158,819 | 10/1992 | Goodman, Jr. et al. | 604/385.1 X |

FOREIGN PATENT DOCUMENTS

| | | |
|---|---|---|
| 0523683A1 | 7/1992 | European Pat. Off. . |
| 0523719A1 | 7/1992 | European Pat. Off. . |

*Primary Examiner*—David Brown

[57] ABSTRACT

An absorbent article such as a sanitary napkin having an improved topsheet that provides improved skin comfort as well as superior fluid handling characteristics. Such absorbent articles comprise a liquid pervious topsheet, a liquid impervious backsheet, and an absorbent core positioned between the topsheet and the backsheet. The topsheet has a central zone and an outer zone extending laterally outwardly from and contiguous with the central zone. The topsheet comprises an outer portion located substantially in the outer zone and a central portion located substantially in the central zone. The outer portion includes a microapertured polymeric web which exhibits a soft and silky tactile impression. The central portion includes a macroscopically-expanded, apertured formed-film for the transmission of bodily fluids deposited on the topsheet.

13 Claims, 8 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

ABSORBENT ARTICLE WITH MULTI-FUNCTIONAL TOPSHEET

FIELD OF THE INVENTION

The present invention relates to absorbent articles such as sanitary napkins, adult incontinence pads, and the like, and more particularly, the present invention relates to a multi-functional topsheet suitable for use on absorbent articles which provides excellent fluid acquisition and skin comfort.

BACKGROUND OF THE INVENTION

All manner and variety of absorbent articles configured for the absorption of bodily fluids such as menses, urine, and feces are, of course, well known. Generally, absorbent articles comprise a liquid pervious topsheet, a liquid impervious backsheet, and an absorbent core positioned between the topsheet and the backsheet. The exudates from a wearer's body readily penetrates through the topsheet and are contained in the absorbent core.

The topsheet serves a multiplicity of purposes. The first function of the topsheet is to provide fluid acquisition and retention for the absorbent product. Secondly, since the topsheet is the wearer contacting surface of the absorbent product, it should present a user friendly surface (both visual and tactile) prior to, during and after use.

There are a number of topsheet executions which have attempted to optimize one or more of these topsheet functions. Three-dimensional, macroscopically expanded, apertured formed-films have been preferred for their ability to efficiently perform the first function, fluid acquisition and retention. Formed-film topsheets of this type are available in the market place and are described in U.S. Pat. No. 3,929,135 issued to Thompson on Dec. 30, 1975; U.S. Pat. No. 4,324,426 issued to Mullane et al. on Apr. 13, 1982; U.S. Pat. No. 4,324,314 issued to Radel et al. on Aug. 3, 1982; and U.S. Pat. No. 4,463,045 issued to Ahr, et al. on Jul. 31, 1984, all of which are herein incorporated by reference. The formed-films described in these patents are generally recognized and consumer appreciated for their superior fluid handling ability. However, in spite of their superior fluid handling ability, these structures are considered somewhat deficient by some users, compared to fiber based topsheets, in their performance of the second function, i.e., providing a user friendly surface.

There have been numerous efforts to make formed-film webs suitable for use as topsheets which more effectively address this second function of the topsheet, i.e., providing a user friendly surface. Formed-film webs having user friendly surfaces are described in U.S. Pat. No. 4,609,518 issued to Curro et al. on Sep. 2, 1986; and U.S. Pat. No. 4,629,643 issued to Curro et al. on Dec. 16, 1986, both of which are herein incorporated by reference. Webs of the type described in these patents are generally perceived as clothlike and comparable to fiber based webs in their performance of providing a user friendly surface. However, although they are superior to fiber based webs for fluid handling, they are somewhat deficient in fluid handling when compared to the three-dimensional, macroscopically expanded, apertured formed-film webs described earlier.

Formed-films of both types just described above have been used as topsheets on various disposable absorbent articles. However, as just illustrated, the choice of a topsheet is based on a compromise between the two fundamental topsheet functions, superior fluid handling and a user friendly surface. In the past it has been possible to optimize one or the other but generally not both superior fluid handling and a user friendly surface at the same time.

SUMMARY OF THE INVENTION

The present invention pertains, in a preferred embodiment, to absorbent articles such as sanitary napkins, pantiliners, adult incontinence pads, and the like. The absorbent article includes a liquid pervious topsheet having two or more zones which have been specifically designed to optimally perform different functions. For example, one preferred embodiment has a central zone and an outer zone extending outwardly from and contiguous with the central zone. The topsheet includes an outer portion located substantially in the outer zone. The outer portion includes formed-film webs specifically designed to optimize the second function of the topsheet, i.e., providing a skin friendly surface. Preferably, the outer portion includes a microapertured polymeric web exhibiting a soft and silky tactile impression. The topsheet also includes a central portion located substantially in the central zone. The central portion comprises a formed-film web designed primarily to optimize the first function of the topsheet, i.e., the fluid handling function of the topsheet. Preferably, the central portion comprises a macroscopically-expanded, three-dimensional, apertured formed-film for the transmission of bodily fluids deposited on the topsheet. A liquid impervious backsheet is joined to the topsheet. An absorbent core having side edges is positioned between the topsheet and the backsheet.

In a particularly preferred embodiment, the topsheet is made of a single unitary of polymeric material web.

In a preferred embodiment, the outer zone of the topsheet may include a first outer portion and a second outer portion laterally coextensive to the first outer portion. The second outer portion may serve as a backsheet if the web is wrapped around the absorbent core.

In another embodiment, the outer portion includes two strips of polymeric film secured to the central portion. Preferably, the outer portion is secured to the central portion by fusion bonding.

The absorbent core is preferably positioned below the central zone and the outer zone. Preferably, the apertured thermoplastic film layer and the absorbent core are laterally coextensive.

In a preferred embodiment, the absorbent article comprises a pair of flaps extending laterally outward from the side edges of the absorbent core. Each flap includes a portion of the topsheet and the backsheet and each said flap includes the outer portion of the topsheet.

BRIEF DESCRIPTION OF THE DRAWINGS

While the specification concludes with claims particularly pointing out and distinctly claiming the present invention, it is believed that the present invention will be better understood from the following description in conjunction with the accompanying drawings, in which like reference numbers identify identical elements and wherein:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad.

Figure 1:
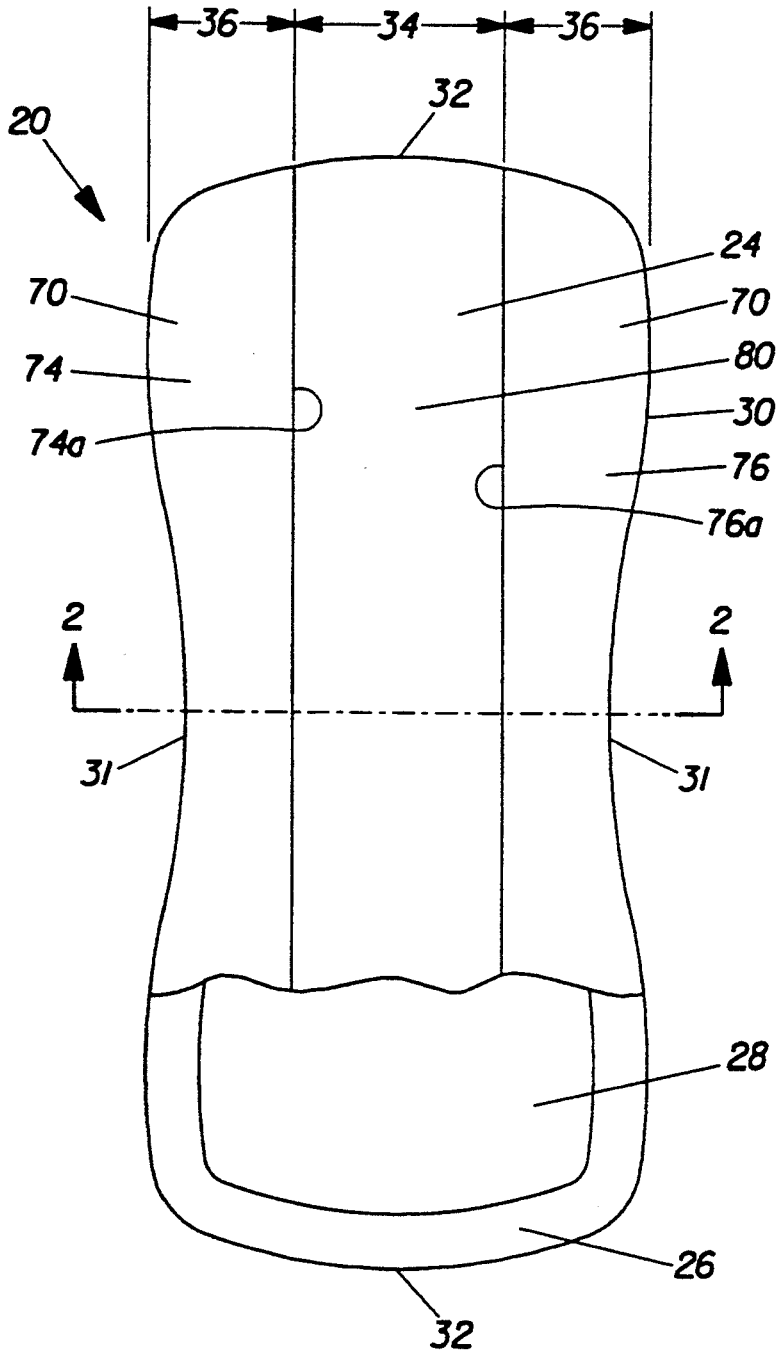
FIG. 1 is a top plan view of a preferred sanitary napkin of the present invention with portions cut-away to more clearly show the construction of the sanitary napkin.

A preferred embodiment of a unitary disposable absorbent article of the present invention is the catamenial pad, sanitary napkin 20, shown in FIG. 1. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). Interlabial devices which reside partially within and partially external of the wearer's vestibule are also within the scope of this invention. As used herein, the term "pudendal" refers to the externally visible female genitalia. It should be understood, however, that the present invention is also applicable to other feminine hygiene or catamenial pads such as pantiliners, or other absorbent articles such as incontinence pads, and the like.

The sanitary napkin 20 has two surfaces, a body-contacting surface or "body surface" and a garment surface. The sanitary napkin 20 is shown in FIG. 1 as viewed from its body surface. The body surface is intended to be worn adjacent to the body of the wearer while the garment surface is on the opposite side and is intended to be placed adjacent to the wearer's undergarments when the sanitary napkin 20 is worn.

The sanitary napkin 20 has two centerlines, a longitudinal centerline and a transverse centerline. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable, and refer to a line, axis or direction which lies within the plane of the sanitary napkin 20 that is generally perpendicular to the longitudinal direction.

FIG. 1 is a top plan view of the sanitary napkin 20 of the present invention in its flat-out state with portions of the structure being cut-away to more clearly show the construction of the sanitary napkin 20 and with the portion of the sanitary napkin 20 which faces or contacts the wearer, oriented towards the viewer. As shown in FIG. 1, the sanitary napkin 20 preferably comprises a liquid pervious multi-zone topsheet 24, a liquid impervious backsheet 26 joined with the topsheet 24, and an absorbent core 28 positioned between the topsheet 24 and the backsheet 26. The multi-zone topsheet 24 has a central zone 34 and an outer zone 36. The outer zones 36 extend laterally from and are contiguous with the central zone 34.

FIG. 1 also shows that the sanitary napkin 20 has a periphery 30 which is defined by the outer edges of the sanitary napkin 20 in which the longitudinal edges or ("side edges") are designated 31 and the end edges (or "ends") are designated 32.

Figure 2:
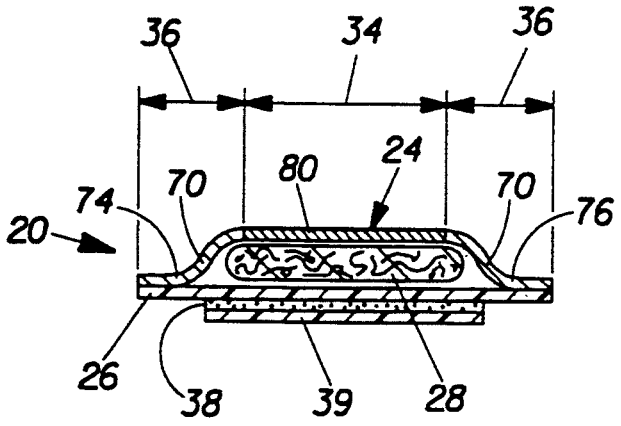
FIG. 2 is a cross-sectional view of the sanitary napkin of FIG. 1 taken along section line 2—2.

FIG. 2 is a cross-sectional view of the sanitary napkin 20 taken along section line 2—2 of FIG. 1. FIG. 2 shows the adhesive fastening means 38 for attaching the sanitary napkin 20 to the undergarment of the wearer. Removable release liner 39 covers the adhesive fastening means 38 to keep it from sticking to a surface other than the crotch portion of the undergarment prior to use.

The multi-zone topsheet 24 comprises an outer portion 70 and a central portion 80. The outer portion 70 is generally located in the outer zone 36 of the topsheet 24. The outer portion 70 of topsheet 24 provides the second function for the topsheet, i.e., provides a user friendly surface. The central portion 80 is generally located in the central zone 38 of the topsheet 24. The central portion 80 provides the first function for the topsheet, i.e., fluid acquisition and retention.

The primary function of the central portion of the topsheet is fluid acquisition and retention while the primary function of the outer portion is to provide a user friendly surface. While the primary functions of each portion of the topsheet have been established they may also preform other functions. For example, the outer portion while maintaining a user friendly surface may have the ability to provide some fluid acquisition and retention functions. However, when compared to the fluid acquisition and retention capabilities of the central portion, the outer portion in no way performs these functions as well as the central portion of the topsheet. Because the outer portion may serve the primary function of providing a user friendly surface and a secondary function of fluid handling, the distinction between the central zone and the outer zone of the topsheet may not be readily apparent. However, one merely has to look at or feel the user friendly surface or the lack thereof to distinguish between the central zone and the outer zone. The central zone will not have the additional elements which create a user friendly surface, e.g., a plurality of microapertured surface aberrations, whereas the outer zone will have these elements. That is not to say that the central zone of the topsheet will not be made as user friendly as possible. It simply means that the fluid handling ability of the central zone will not be compromised in order to provide a user friendly surface as is done with the outer zone of the topsheet.

In a preferred embodiment, illustrated in FIGS. 1 and 2, the outer portion 70 comprises two strips 74, 76. The two strips 74, 76 of the outer portion 70 are spaced apart on either side of the central portion 80. In this particular embodiment, each strip 74, 76 has approximately parallel inner edges 74*a*, 76*a* being spaced apart from one end edge 32 to the other end edge 32 whereby the central portion 80 has a substantially rectangular shape elongated in the longitudinal direction.

The outer portion 70 covers the outer zones 36. The central portion 80 is positioned between the outer portions 70 and lies within the central zone 34 between the end edges 32. While the central portion 80 need not extend to the end or longitudinal edges of the sanitary napkin, in a preferred embodiment as shown in FIG. 1, the central portion 80 extends laterally and longitudinally outward and can form a portion of the longitudinal edges 31 and the end edges 32.

Figure 8:
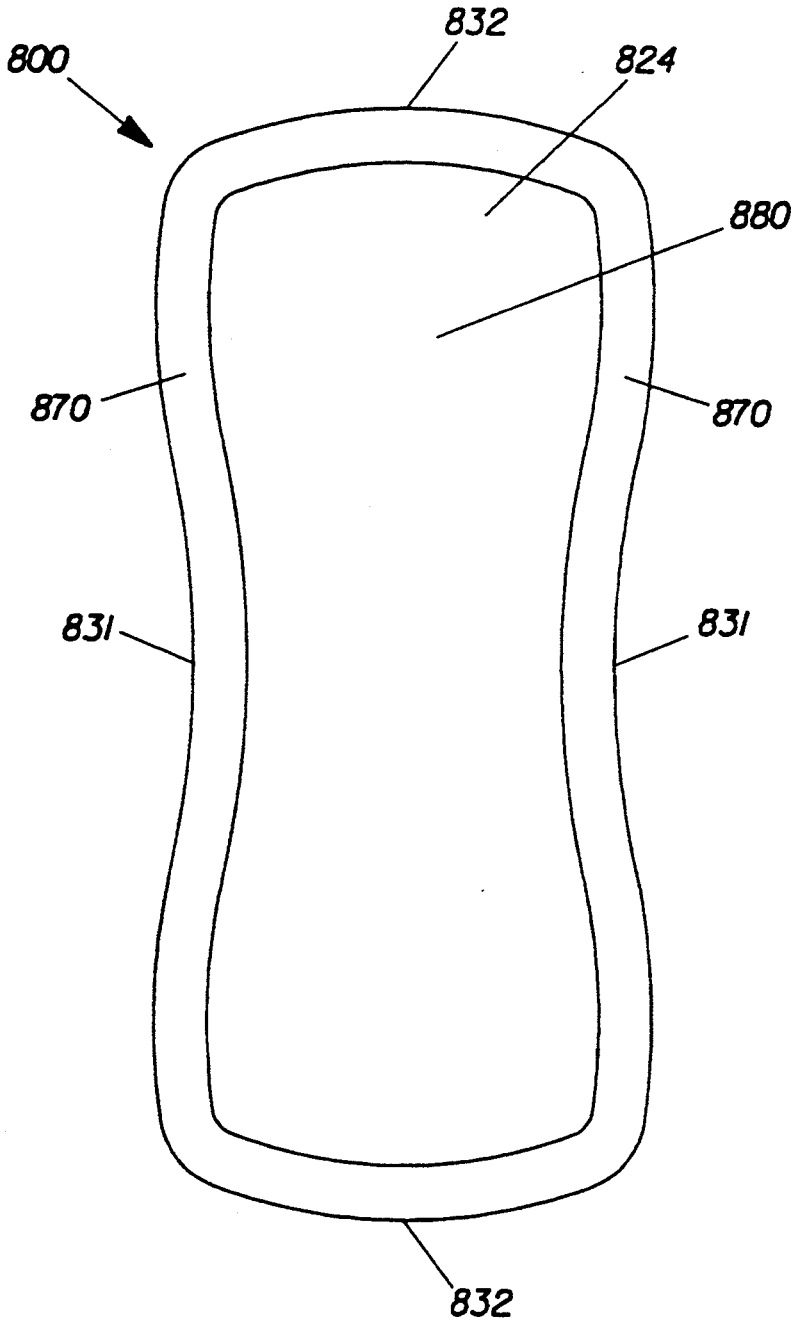
FIG. 8 is a top plan view of another preferred embodiment of a sanitary napkin of the present invention.

As long as the central portion 80, located generally in the central zone 34, is sufficiently large enough to permit the flow of bodily fluids intended to be absorbed by the absorbent core 28, the longitudinal ends of the central zone 34 may be covered with the outer portion 70, as shown in FIG. 8. Referring now to FIG. 8, the sanitary napkin 800 has an overall shape generally similar to that of the sanitary napkin 20 illustrated in FIG. 1. However, unlike the sanitary napkin 20 illustrated in FIG. 1, the outer portion 870 of sanitary napkin 800 not only covers the longitudinal portions adjacent the longitudinal edge 831 of the sanitary napkin 800, but also covers the ends of the sanitary napkin 800 adjacent the end edges 832. Accordingly, the central portion 880 of the topsheet 824 is completely surrounded about its periphery by the outer portion 870.

Referring now to FIG. 1, a preferred sanitary napkin 20 has concave longitudinal edges 31 to fit the contour of the wearer's panty. In this embodiment, the outer portion 70 has a width of at least about 1.5 mm in both outer zones at the narrowest portion and about at least 7–10 mm at the widest portion. The width of the central portion 80 will depend upon the intended use of the article. For low-flow sanitary napkins the width of the central portion is greater than about 5 mm, preferably about 10 mm to about 30 mm, and most preferably about 20 mm. For heavier-flow sanitary napkins, the width of the central portion is more than about 10 mm, preferably about 20–60 mm, and most preferably about 40 mm. The ratio of the width of the central portion 80 to the total the lateral width of the remainder of the sanitary napkin can vary based on the width of the outer portion 70. The ratio is preferably about 4:1 to about 1:4, more preferably from about 2:1 to about 1:2. It has been found that such shapes and area for the central portion 80 are desirable from a product performance, process, and aesthetic standpoint. However, other shapes and various areas are possible in the design of the central portion 80. For example, each strip 74, 76 can have a non-parallel edge, or can meet at or inward from either or both longitudinal edges 31 to define a circular central portion. In addition, the central portion may have a variety of shapes, such as oval, oblong, elliptical, dog-bone, diamond, triangular, etc. So long as the central portion is sufficiently large to permit passage of most of the fluids deposited onto the topsheet 24 to the absorbent core, the particular arrangement, configuration, or shape of the central portion is not critical.

In a particularly preferred embodiment, shown in FIG. 2, the outer portion 70 and the central portion 80 are formed from a unitary web of thermoplastic material. Therefore, no separate bonding, attachment or securement means is required to secure the outer portion 70 to the central portion 80.

Alternatively, the outer portion 70 and the central portion 80 may be comprised of separate webs secured to one another. The outer portion 70 may be secured to the central portion 80 such that the edges of the webs abut one another. This would result in a topsheet similar to that of FIG. 2 except that the outer portion 70 would be secured to the central portion 80 by fusion bonding, adhesive attachment of the layers, or by any other securement means. The bonding of the outer portion 70 to the central portion 80 can prevent the outer portion 70 from being torn or from rolling back onto itself at edges 74*a*, 76*a* thereby imparting an uncomfortable feeling. Fusion bonding includes heat bonding, ultrasonic bonding and the like. Heat bonding is the preferred means for securing the outer portion 70 and the central portion 80 in contacting relation. The two layers can be continuously, partially, or intermittently bonded together.

Figure 2A:
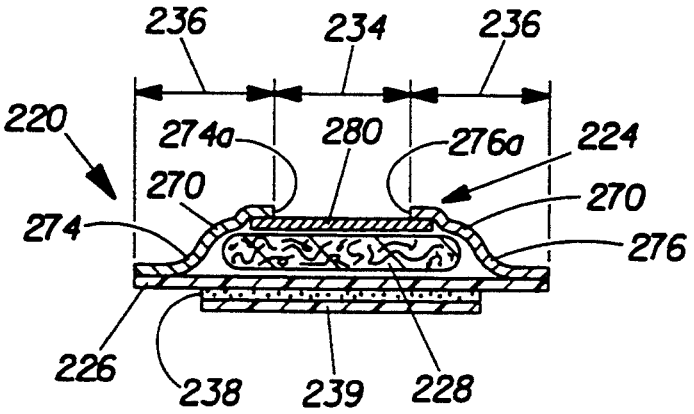
FIG. 2A is a cross-sectional view of another preferred embodiment of the sanitary napkin of the present invention.

Referring now to FIG. 2A, another preferred embodiment of a sanitary napkin 220 is illustrated. The sanitary napkin 220 preferably comprises a liquid pervious topsheet 224, a liquid impervious backsheet 226 joined with topsheet 224, and an absorbent core 228 positioned between the topsheet 224 and the backsheet 226. The sanitary napkin has an adhesive fastening means 238 secured to the backsheet 226 and removable release liner 239 covering the adhesive fastening means 238. The topsheet 224 has a central zone 234 and an outer zone 236. The topsheet 224 comprises an outer portion 270 and the central portion 280. The outer portion 270 is generally located in the outer zone 236 and a central portion 280 is generally located in the central zone 238. The outer portion 270 is comprised of two strips 274, 276. The two strips 274, 276 of the outer portion 270 are spaced apart and on top of the central portion 280. In this configuration the topsheet 224 is comprised of three separate portions, i.e., the two outer portions and the central portion, bonded together by any of the methods mentioned above. The outer portion 270 and the central portion 280 are spot-bonded at a plurality of positions along the inner edge 274*a*, 276*a* of each strip 274, 276 respectively with a heat bond. The heat bond provides an embossed seal pattern that can also convey an aesthetic effect on its pattern such as a flower, a leaf, and the like.

Figure 2B:
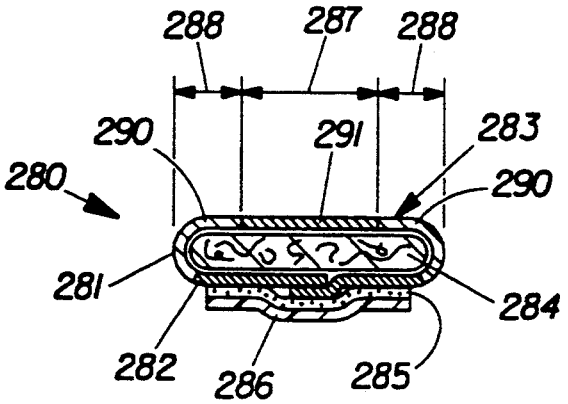
FIG. 2B is a cross-sectional view of another preferred embodiment of the sanitary napkin of the present invention.

Referring now to FIG. 2B, another preferred embodiment of a sanitary napkin 280 is illustrated. The sanitary napkin 280 comprises a unitary web 281 which forms a portion of the topsheet 283 and the backsheet 282. The topsheet portion 283 of unitary web 281 has a central zone 287 and an outer zone 288. The topsheet has an outer portion 290 and a central portion 291. The outer portion 290 is generally located in the outer zone 288. The central portion 291 is generally located in the central zone 287. A liquid impervious backsheet portion 282 forms a portion of the unitary web 281. The unitary web 281 is sealed together along the edges of the backsheet portion 282 to form the tubular like structure of the sanitary napkin 280. An absorbent core 284 is positioned within the tubular structure and between the topsheet portion 283 and the backsheet portion 282 of the unitary web 281. An adhesive fastening means 285 is secured to the backsheet portion 282 of the sanitary napkin 280. Removable release liner 286 covers the adhesive fastening means 285 to keep it from sticking to a surface other then the crotch portion of the undergarment prior to use.

Figure 3:
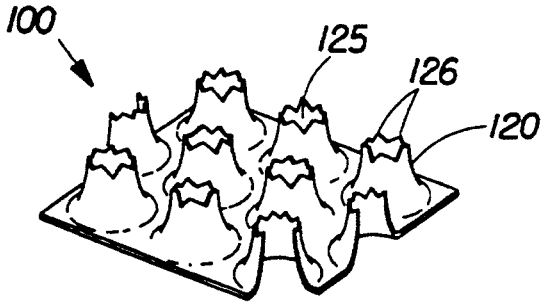
FIG. 3 is a greatly enlarged, simplified, perspective illustration of a segment of a microapertured "planar" web of the type generally disclosed in U.S. Pat. No. 4,629,643 issued to Curro et al. on Dec. 16, 1986.

As mentioned earlier herein, the outer portion provides the user friendly function of the topsheet. Preferably, the outer portion comprises a microapertured polymeric web which exhibits a soft and silky tactile impression. An example of such a structure is disclosed in U.S. Pat. No. 4,629,643 issued to Curro et al. on Dec. 16, 1986, which is incorporated herein by reference. FIG. 3 is a greatly enlarged perspective illustration of a segment of a "planar" microapertured web 100 generally in accordance with the teachings of Curro et al. The term "planar", as used herein refers to the overall condition of the web, ribbon or film when viewed by the normal naked eye on a macroscopic scale. In this context "planar" webs, ribbons and films may include webs, ribbons and films having a fine scale, yet visible, pattern of surface aberrations on one or both sides thereof, the surface aberrations comprising said visible pattern not being individually discernible to the normal naked eye when the perpendicular distance between the viewer's eye and the plane of the web is about 12 inches. As can be seen from FIG. 3, the soft and silky feeling web 100 exhibits a pattern of discrete volcano-like surface aberrations 120. Each of the surface aberrations 120 has its amplitude oriented substantially perpendicular to the surface in which the surface aberration originates. An aperture 125 is provided substantially coincidental with the maximum amplitude of each surface aberration 120. In addition, the volcano-like apertures are typically in the form of a thin, irregularly shaped petals 126.

The existence of the microapertures 125 at the center of each of the surface aberrations 120 greatly reduces the resistance to collapse of each of the individual surface aberrations 120. In addition, the irregular nature of the petals 126 formed about the periphery of microapertures 125, and the pliable nature of the thinned petals 126 contribute to the soft and silky tactile perception of the microapertured polymeric "planar" web 100.

In a particularly preferred embodiment, the microapertured "planar" web 100, forming the outer portion of the topsheet, is "macroscopically expanded" to form a three-dimensional polymeric web. The term "macroscopically expanded", as used herein refers to webs, ribbons and films which have been caused to conform to the surface of a three-dimensional forming structure so that both surfaces thereof exhibit a three-dimensional pattern of surface aberrations corresponding to the macroscopic cross-section of said forming structure, the surface aberrations comprising said patterns being individually discernible to the normal naked eye, i.e., a normal eye having 20/20 vision unaided by any instrument that changes the appearance, size or distance of an object or otherwise alters the visual powers of the eye, when the perpendicular distance between the viewers eye and the plane of the web is about 12 inches. Such macroscopically expanded webs, ribbons and films are typically caused to conform to the surface of said forming structure by embossing, i.e., when the forming structure exhibits a pattern comprised of primarily of male projections, by debossing, i.e., when the forming structure exhibits a pattern comprised of primarily female capillary networks, or by extrusion of a resinous melt directly onto the surface of a forming structure of either type.

Figure 4:
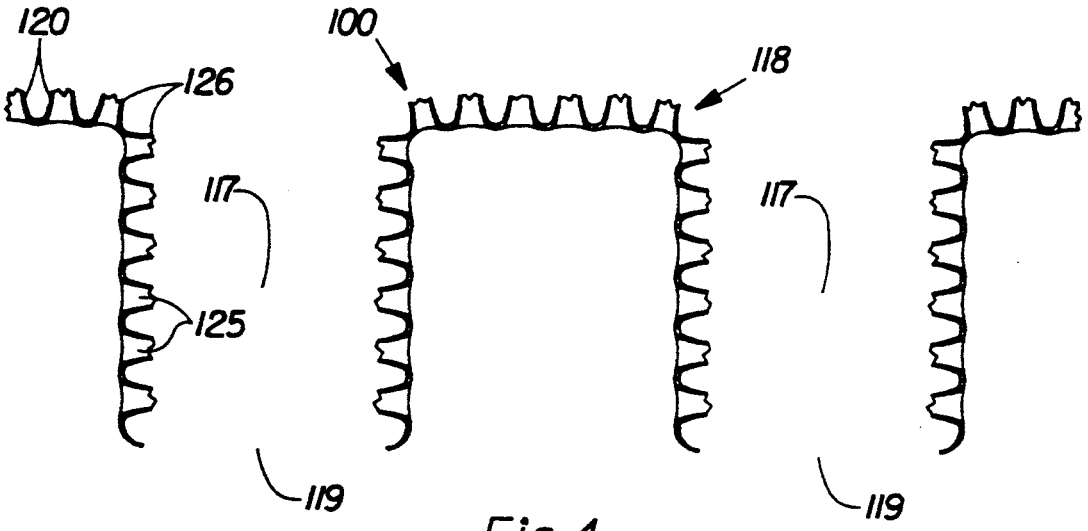
FIG. 4 is a greatly enlarged simplified cross-sectional illustration of a "macroscopically expanded", macroscopically apertured three-dimensional web formed using a "planar" web of FIG. 3 as a starting material.

Exemplary "macroscopically expanded" webs are those generally taught in U.S. Pat. No. 4,342,314 issued to Radel et al. on Aug. 3, 1982, said patent being hereby incorporated herein by reference. Macroscopic expansion is preferably carried out by orienting the microapertured surface aberrations 120 so that microapertures 125 form the skin contacting surface of the macroscopically expanded web 118, as generally shown in FIG. 4. The resilience imparted by macroscopic expansion of the web is superposed on that exhibited by the microapertured surface aberrations 120 of "planar" web 100.

Macroscopic debossments 117 in web 118 may be of any particular shape and size desired by creating a forming structure as generally taught by commonly assigned U.S. Pat. No. 4,395,215 issued to Bishop on Jul. 26, 1983 and hereby incorporated herein by reference. The end walls of the debossments 117 have been ruptured to form macroscopic apertures 119. This may be accomplished by using a forming structure of the type disclosed in the aforementioned commonly assigned U.S. Pat. No. 4,342,314 issued to Radel et al., which is incorporated herein by reference.

Figure 5:
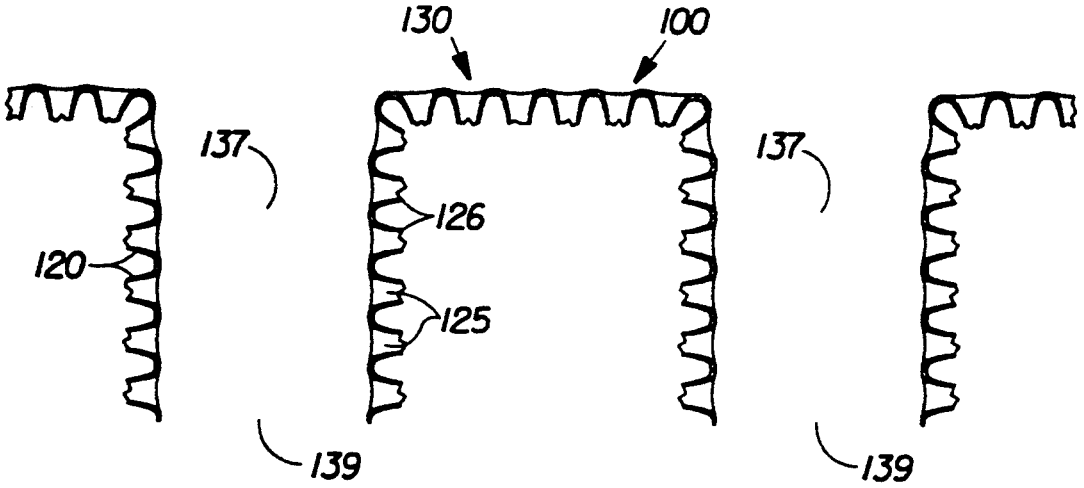
FIG. 5 is a view generally similar to that of FIG. 4, but showing an alternative embodiment of a "macroscopically expanded", macroscopically apertured three-dimensional web formed using a "planar" web as shown in FIG. 3.

The web 130 shown in FIG. 5 exhibits a macroscopic cross-section generally similar to that of web 118, shown in FIG. 4. The end walls of macroscopic debossments 137 have been ruptured to form macroscopic apertures 139. Furthermore, the "planar" web 100 used to form macroscopically expanded web 118 is used to form macroscopically expanded web 130. However, web 130 exhibits a different tactile response, particularly when one touches the non-debossed land areas of the web. This is because of the difference in orientation of the volcano-like surface aberrations 120. The microapertured surface aberrations 120 of web 130 are oriented so that microapertured surface aberrations 120 face inwardly and form the pad contacting surface of the macroscopically expanded web 120.

The process for producing the webs shown in FIGS. 4 and 5 is disclosed in commonly assigned U.S. Pat. No. 4,609,518 issued to Curro et al. on Sep. 2, 1986 which is incorporated herein by reference.

Macroscopically-expanded, apertured formed-films are preferred for the central portion 80 because they are pervious to liquids and yet non-absorbent. Thus, the surface of the macroscopically-expanded, apertured formed-film which is in contact with the body remains dry and is comfortable to the wearer. Suitable macroscopically-expanded, apertured formed-films are described in U.S. Pat. No. 3,929,135 issued to Thompson on Dec. 30, 1975; U.S. Pat. No. 4,324,426 issued to Mullane et al. on Apr. 13, 1982; U.S. Pat. No. 4,342,314 issued to Radel et al. on Aug. 3, 1982; and U.S. Pat. No. 4,463,045 issued to Ahr, et al. on Jul. 31, 1984. Each patent is incorporated herein by reference.

Figure 9:
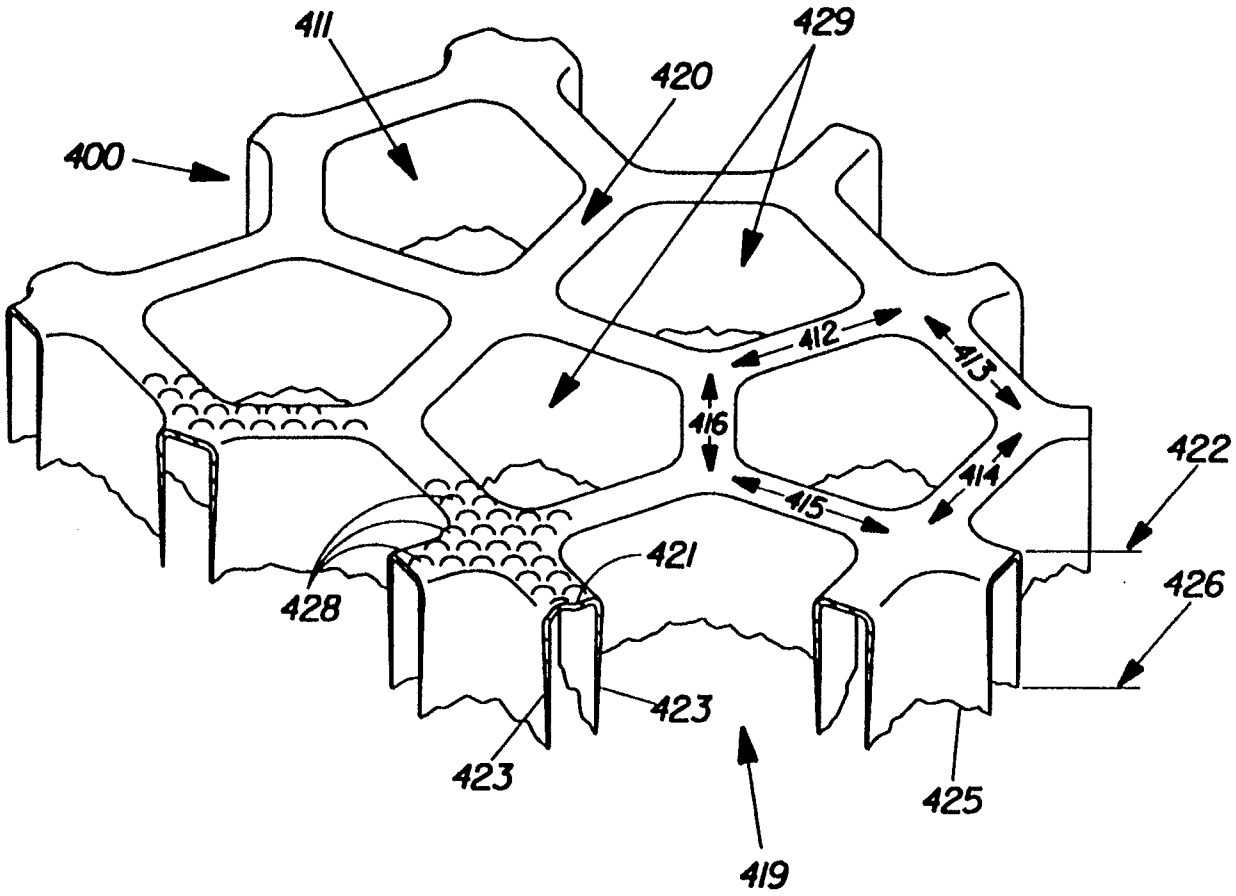
FIG. 9 is an enlarged partially segmented, perspective illustration of a prior art macroscopically expanded, apertured formed-film plastic web of the type generally disclosed in commonly assigned U.S. Pat. No. 4,342,314, said web further exhibiting a microscopic pattern of surface aberrations of the type generally disclosed in commonly assigned U.S. Pat. No. 4,463,045 on its visible surface.

In a particularly preferred embodiment of the present invention, the central portion 80 is comprised of the macroscopically, expanded, apertured formed-film 400 illustrated in FIG. 9. The macroscopically, expanded, apertured formed-film 400 is generally in accordance with the teachings of commonly assigned U.S. Pat. No. 4,342,314 issued to Radel et al. on Aug. 3, 1982. The macroscopically, expanded, apertured formed-film 400 illustrated in FIG. 9 exhibits a multiplicity of apertures, e.g., apertures 411, which are formed by a multiplicity of intersecting fiber-like elements, e.g., elements 412, 413, 414, 415 and 416, interconnected to one another in the first surface 420 of the formed-film web. Each fiber-like element comprises a base portion, e.g., base portion 421, located in plane 422. Each base portion has a sidewall portion, e.g., sidewall portions 423, attached to each edge thereof. The sidewall portion extends generally in the direction of the second surface 425 of the web. The intersecting sidewall portions of the fiber-like elements are interconnected to one another intermediate the first and second surfaces of the web, terminating substantially concurrently with one another in the plane 426 of the second surface. Preferably, the interconnected sidewall portions 423 terminate substantially concurrently with one another in the plane of the second surface to form apertures 419 in the second surface 425 of the web. The capillary network 429 formed by the interconnected sidewall portions allows for free transfer of fluids from the first surface of the web directly to the second of the web without lateral transmission of the fluid between adjacent capillary networks.

In a particularly preferred embodiment, the base portion 421 includes a microscopic pattern of surface aberrations 428, generally in accordance with teachings of commonly assigned U.S. Pat. No. 4,463,045 issued to Ahr et al. on Jul. 31, 1984. The microscopic pattern of surface aberrations 428 provides a substantially non-glossy visible surface when the web is struck by incident light rays.

In a preferred embodiment of the present invention, the body surface of the central, macroscopically expanded, apertured formed-film portion 80 is hydrophilic so as to help liquid transfer through the central portion 80 faster than if the body surface was not hydrophilic. This will diminish the likelihood that menstral fluid will flow off the topsheet rather than following into and being absorbed by the absorbent core. In a preferred embodiment, surfactant is incorporated into the polymeric material of the central formed-film portion 80 such as described in U.S. patent application Ser. No. 7/794,745 entitled "Absorbent Article Having a Nonwoven Apertured Film Cover Sheet" filed on Nov. 19, 1991 by Aziz, et al. Alternatively, the body surface of the central portion 80 can be made hydrophilic by treating it with a surfactant such as described in U.S. Pat. No. 4,950,264 issued to Osborn on Aug. 21, 1991 and U.S. Pat. No. 5,009,653 issued to Osborn on Apr. 23, 1991 both of which are incorporated herein by reference.

Figure 6B:
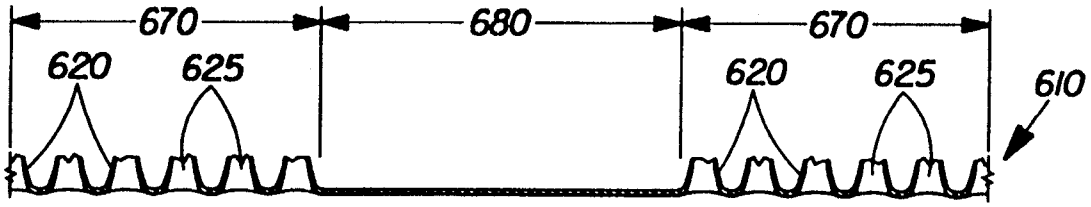
FIG. 6B is a greatly enlarged, cross-sectional inset of the web shown in FIG. 6 while it is still in "planar" condition.
Figure 6:
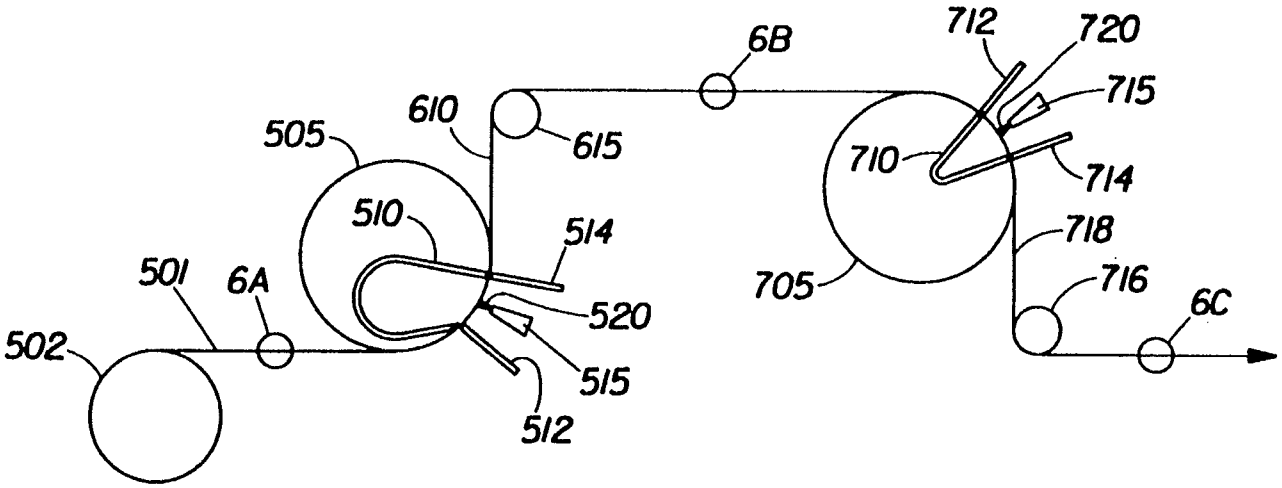
FIG. 6 is a greatly simplified schematic illustration of a preferred process for forming a unitary web suitable for use as the topsheet of the present invention.

In a particularly preferred embodiment of the present invention the topsheet 24 is preferably of a unitary construction. That is, outer portion 70 and central portion 80 are made of a single web such that no seaming and or fusing is required to join the outer portion 70 to the central portion 80. FIG. 6 is a simplified schematic illustration of a particularly preferred process for forming a unitary polymeric web containing a pattern of microapertured surface aberrations on the outer portion 70 and "macroscopically expanded" three-dimensional apertures in the central portion 80 of the topsheet 24. In a particularly preferred process the outer portion 70 in addition to being microapertured is also formed into a "macroscopically expanded" structure similar to that of the central portion 80.

Figure 6A:
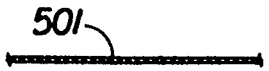
FIG. 6A is a greatly enlarged, cross-sectional inset of the web shown in FIG. 6 prior to any processing.

In particular, a web of substantially smooth flat polymeric material 501 is fed from a supply roll 502 onto the surface of a woven wire support member 505 which rotates about a stationary vacuum chamber 510. The cross-section of the incoming web 501 is shown in greatly enlarged form in the inset of FIG. 6A. A high pressure liquid jet nozzle 515 is directed to a portion of the exposed surface of a substantially smooth flat film 501 intermediate a pair of baffles 512, 514 as the web traverses the vacuum chamber. The high pressure, i.e., preferably at least about 800 psig jet of liquid 520 causes the smooth flat web 501 to assume the general contour of the knuckle pattern of the woven wire support member 505. In addition, because the intricacies formed by the intersecting filaments are unsupported, the fluid jet causes rupture at those portions of web 501 coinciding with the interstices in the woven wire support structure 505, thereby producing a "planar" microapertured web 610 in those portions corresponding with fluid nozzle jet 515, a segment of which is shown in greatly enlarged form in the inset of FIG. 6B. A portion of the web 610 exhibits a multiplicity of fine scale surface aberrations 620 generally similarly aberrations 120 of web 100. The microapertures 625 coincide with the point of maximum amplitude of the surface aberrations 620. Thus, portions of web 610 are substantially identical to web 100 shown generally in FIGS. 4 and 5. It should be understood that the central portion 680 of web 610 corresponds with the central portion 80 of the topsheet 24 while the outer portions 670 generally correspond with the outer portions 70 of the topsheet 24.

The web 610 is removed from the surface of woven wire forming structure 505 and passed about idler roll 615.

The web 610 is forwarded with surface aberrations 620 generally outwardly oriented about the periphery of a macroscopic patterned three-dimensional forming structure 705 which rotates about a second stationary vacuum chamber 710. A second high pressured liquid nozzle 715 is located intermediate stationary baffles 712, 714. High pressure liquid nozzle 715 applies a high pressure, i.e., preferably at least about 400 psig, liquid jet 720 substantially across the entire width of "planar" web 610. The high pressure liquid jet 720 causes macroscopic expansion of the "planar" web 610 to a three-dimensional configuration generally resembling that of the forming structure 705 prior to removal about idler roll 716.

Figure 6C:
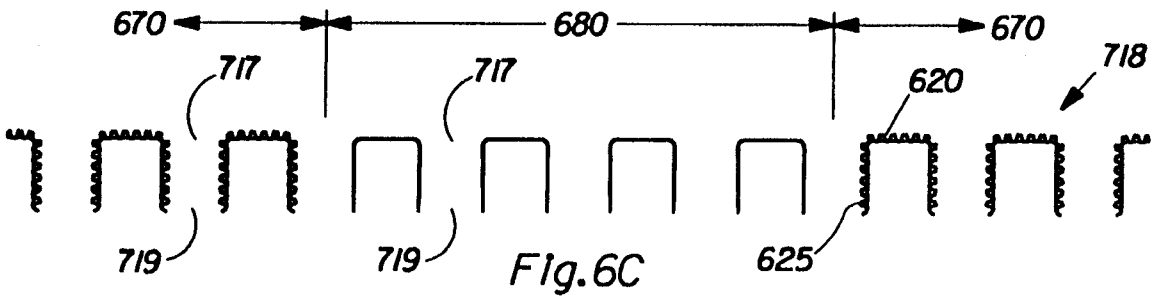
FIG. 6C is a greatly enlarged inset of the multi-zone web shown in FIG. 6 after it has been macroscopically expanded, macroscopically and microscopically apertured.
Figure 6D:
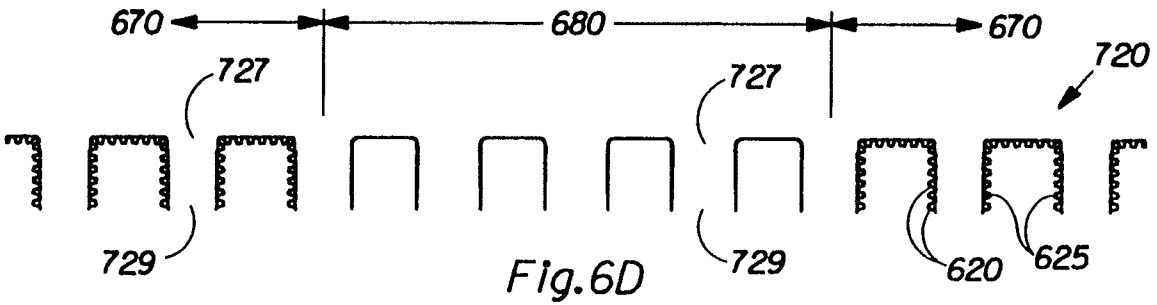
FIG. 6D is a greatly enlarged, cross-sectional view of a segment of an alternative embodiment of a macroscopically expanded, macroscopically and microscopically apertured multi-zone web of the present invention.

A greatly enlarged segment of the resulting macroscopically expanded and macroscopically apertured multi-zone web 718 is shown in the inset of FIG. 6C. The macroscopically expanded web 718 exhibits a multiplicity of debossments 717 each having a macroscopic aperture 719 located at its lowermost end. The microapertured surface aberrations 620, located in the outer portion 670, are outwardly oriented during the macroscopic expansion process so that the skin contacting surface of the macroscopically expanded web 718 comprises the edges of the microapertures 625 formed in each of the surface aberrations 620.

A greatly enlarged segment of an alternative macroscopically apertured multi-zone web 720 is shown in FIG. 60. The web 720 exhibits a multiplicity of debossments 727 each having a macroscopic aperture 729 located at its lowermost end. The microapertured surface aberrations 620, located in the outer portion 670, are inwardly oriented during the macroscopic expansion process.

Figure 6E:
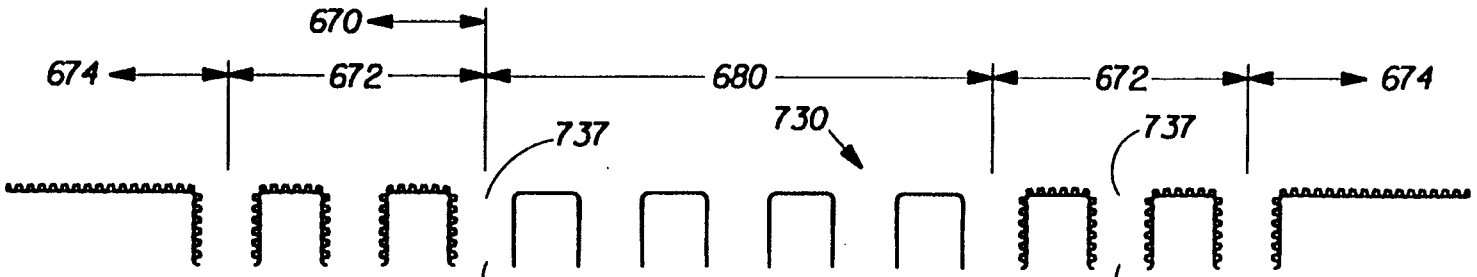
FIGS. 6E is a greatly enlarged, cross-sectional view of a segment of an alternative embodiment of a macroscopically expanded, macroscopically and microscopically apertured multi-zone web of the present invention.

A greatly enlarged segment of another embodiment of a macroscopically apertured multi-zone web 730 is shown in FIG. 6E. The web 730 exhibits a multiplicity of debossments 737 each having a macroscopic aperture 739 located at its lowermost end. The web 730 has a central portion 680 and an outer portion 670. Outer portion 670 is subdivided into a first outer portion 672 and a second outer portion 674. It should be understood that the central portion 680 of web 730 corresponds with the central portion of the topsheet while the outer portion 670 generally corresponds with outer portions of the topsheet on the absorbent article. The microapertured surface aberrations 620 located in the first and second outer portions 672, 674 are outwardly oriented during the macroscopic expansion process so that the skin contacting surface of the macroscopically expanded web 730 comprises the edges of the microapertures 625 formed in each of the surface aberrations 620. The first outer portion 672 has been macroscopically expanded and microapertured. Thus, the first outer portion 672 provides a user friendly surface while maintaining some ability to transmit fluids therethrough. The second outer portion 674 merely has microapertures thereon providing a user friendly surface. The second outer portion 674 may serve as a portion of the topsheet and as the backsheet as it is substantially less pervious to the passage of fluids. For example, the second outer portion may serve as the backsheet 282 on the sanitary napkin 280, illustrated in FIG. 2B, since it has no macroscopic apertures and is therefor substantially impervious to the passage of fluids.

The size of the macroscopic debossments and apertures located in the central portion, and within the outer portion in some embodiments, may be of uniform size throughout the the web. The macroscopic debossments and apertures may also be of uniform size within their respective zones, i.e., the macroscopic debossments and apertures may be or uniform size within the central zone but different from the macroscopic debossments and apertures within the outer zone. The macroscopic apertures and debossments may be of varying size throughout the respective zones, i.e., they may be of a larger size within the central zone and gradually decreasing as they move through the central zone toward the outer zone of the topsheet. The manufacturer has the ability to select various debossment and aperture sizes to produce the desired fluid handling characteristics of the topsheet. For example, the fluid handling characteristics might be selected different for a pantiliner verses a sanitary napkin.

The absorbent core 28 may be any absorbent means which is capable of absorbing or retaining liquids (e.g., menses and/or urine). As shown in FIG. 1, the absorbent core 28 has a body surface, a garment surface, side edges, and end edges. The absorbent core 28 may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these.

The configuration and construction of the absorbent core may also be varied (e.g., the absorbent core may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core should, however, be compatible with the design loading and the intended use of the sanitary napkin. Further, the size and absorbent capacity of the absorbent core may be varied to accommodate different uses such as incontinence pads, pantiliners, regular sanitary napkins, or overnight sanitary napkins.

Exemplary absorbent structures for use as the absorbent core of the present invention are described in U.S. Pat. No. 4,950,264 entitled "Thin, Flexible Sanitary Napkin" issued to Osborn on Aug. 21, 1990; U.S. Pat. No. 4,610,678 entitled "High-Density Absorbent Structures" issued to Weisman et al. on Sep. 9, 1986; U.S. Pat. No. 4,834,735 entitled "High Density Absorbent Members Having Lower Density and Lower Basis Weight Acquisition Zones", issued to Alemany et al. on May 30, 1989; and European Patent Application No. 0 198 683, The Procter & Gamble Company, published Oct. 22, 1986 in the name of Duenk, et al. Each of these patents are incorporated herein by reference.

The backsheet 26 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the sanitary napkin 20 such as pants, pajamas and undergarments. The backsheet 26 may thus comprise a woven or nonwoven material, polymeric films such as thermoplastic films of polyethylene or polypropylene, or composite materials such as a film-coated nonwoven material. Preferably, the backsheet 26 is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Ethyl Corporation, Visqueen Division, of Terre Haute, Indiana, under the designation XP-39385. The backsheet 26 is preferably embossed and/or matte finished to provide a more clothlike appearance. Further, the backsheet 26 may permit vapors to escape from the absorbent core 28 (i.e., breathable) while still preventing exudates from passing through the backsheet 26.

The backsheet 26 and the topsheet 24 are positioned adjacent the garment surface and the body surface, respectively, of the absorbent core 28 and are preferably joined thereto and to each other by attachment means (not shown) such as those well known in the art. For example, the backsheet 26 and/or the topsheet 24 may be secured to the absorbent core 28 or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation H-1258 or H-2031. The attachment means will preferably comprise an open pattern network of filaments of adhesive as is disclosed in U.S. Pat. No. 4,573,986 entitled "Disposable Waste-Containment Garment", which issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

In use, the sanitary napkin 20 can be held in place by any support means or attachment means well-known for such purposes. Preferably, the sanitary napkin is placed in the user's undergarment or panty and secured thereto by a fastener such as an adhesive 38. The adhesive 38 provides a means for securing the sanitary napkin 20 in the crotch portion of the panty. Thus, a portion or all of the outer surface of the backsheet 26 is coated with adhesive. Any adhesive or glue used in the art for such purposes can be used for the adhesive herein, with pressure-sensitive adhesives being preferred. Suitable adhesives are Century A-305-IV manufactured by the Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697. Before the sanitary napkin 20 is placed in use, the pressure-sensitive adhesive 38 is typically covered with a removable release liner 39 in order to keep the adhesive 38 from drying out or adhering to a surface other than the crotch portion of the panty prior to use. Suitable release liners 39 are also described in the above-referenced U.S. Pat. No. 4,917,697. Any commercially available release liners commonly used for such purposes can be utilized herein. Non-limiting examples of suitable release liners are BL30MG-A Silox E1/0 and BL30MG-A Silox 4P/0 both of which are manufactured by the Akrosil Corporation of Menasha, Wis. The sanitary napkin 20 of the present invention is used by removing the release liner 39 and thereafter placing the sanitary napkin 20 in a panty so that the adhesive 38 contacts the panty. The adhesive 38 maintains the sanitary napkin in its position within the panty during use.

Figure 7:
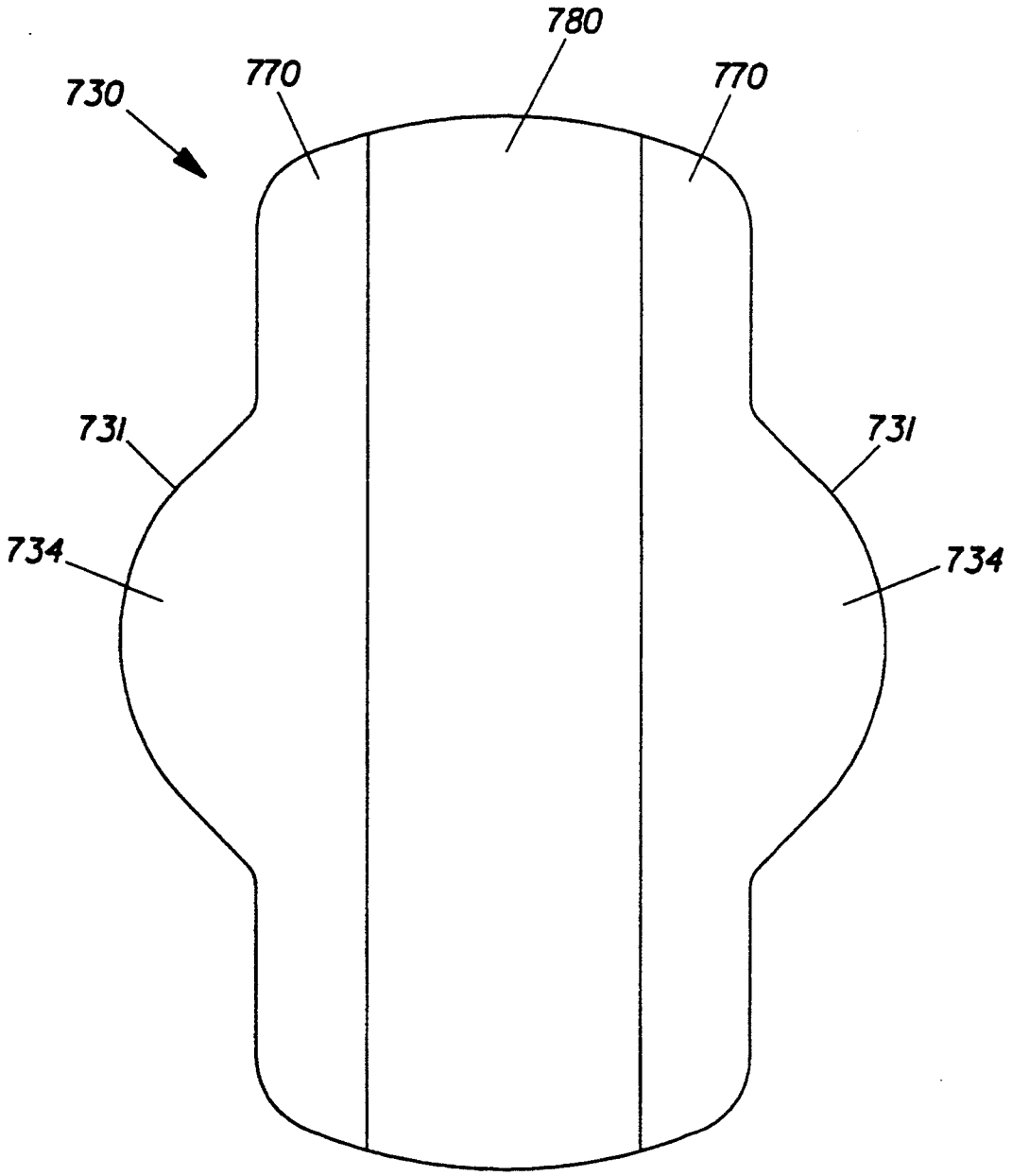
FIG. 7 is a top plan view of another preferred embodiment of a sanitary napkin of the present invention.

Referring now to FIG. 7, the sanitary napkin 730 may also be provided with two flaps 734 each of which are adjacent to and extend laterally from the side edge of the absorbent core. The flaps 734 are configured to drape over the edges of the wearer's panties in the crotch region so that the flaps 734 are disposed between the edges of the wearer's panties and the thighs.

The flaps serve at least two purposes. First, the flaps 734 help serve to prevent soiling of the wearer's body and panties by menstrual fluid, preferably by forming a double wall barrier along the edges of the panty. Second, the flaps 734 are preferably provided with attachment means on their garment surface so that the flaps can be folded back under the panty and attached to the garment facing side of the panty. In this way, the flaps 734 serve to keep the sanitary napkin 720 properly positioned in the panty.

The flaps 734 can be constructed of various materials including materials similar to the topsheet, backsheet, tissue, or combination of these materials. Preferably, the topsheet portion of flaps 734 will be comprised of the same material forming the outer portion 770 of the topsheet and more specifically will be a continuation of the outer portion 770 extending from the central portion 780 to the longitudinal edge of the sanitary napkin 720. The outer portion 770 will be joined with the central portion 780 in a manner similar to that discussed above. Further, the flaps 734 may be a separate element attached to the main body of the napkin or can comprise extensions of the topsheet and backsheet (i.e., unitary). A number of sanitary napkins having flaps suitable or adaptable for use with the sanitary napkins of the present invention are disclosed in U.S. Pat. No. 4,687,478 entitled "Shaped Sanitary Napkin With Flaps", which issued to Van Tilburg on Aug. 18, 1987; U.S. Pat. No. 4,589,876 entitled "Sanitary Napkin", which issued to Van Tilburg on May 20, 1986; and U.S. Pat. No. 4,608,047, entitled "Sanitary Napkin Attachment Means", which issued to Mattingly on Aug. 26, 1986. Each of these patents are incorporated herein by reference.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A multi-zone, unitary, polymeric web having a liquid pervious central zone and an outer zone extending outwardly from and contiguous with said central zone, said web comprising:

(a) a central portion located substantially in said central zone, said central portion including a plurality of macroscopically expanded apertures, said macroscopically expanded apertures transmitting bodily fluid deposited on said web; and (b) an outer portion located substantially in said outer zone, said outer portion including a plurality of microapertures.

2. The multi-zone, unitary, polymeric web of claim 1 wherein said web is a topsheet on an absorbent article.

3. The multi-zone, unitary, polymeric web of claim 1 wherein said outer portion includes a first outer portion and a second outer portion, said second outer portion extends outwardly from and contiguous with said first outer portion.

4. The multi-zone, unitary, polymeric web of claim 3 wherein said first outer portion and said second outer portion form a topsheet on an absorbent article.

5. The multi-zone, unitary, polymeric web of claim 3 wherein said second outer portion forms a backsheet on an absorbent article.

6. An absorbent article comprising:

(a) a liquid pervious, unitary, topsheet having a central zone and an outer zone extending outwardly from and contiguous with said central zone, said topsheet comprising:

(i) a central portion located substantially in said central zone, said central portion including a plurality of macroscopically expanded apertures, said macroscopically expanded apertures transmitting bodily fluids deposited on said topsheet, and (ii) an outer portion located substantially in said outer zone, said outer portion including a plurality of microapertures;

(b) a liquid impervious backsheet joined to said topsheet; and (c) an absorbent core having side edges positioned between said topsheet and said backsheet.

7. The absorbent article of claim 6 wherein said absorbent article is a pantiliner.

8. The absorbent article of claim 6 wherein said absorbent article is a sanitary napkin.

9. The absorbent article of claim 6 wherein said backsheet comprises a microapertured polymeric web.

10. The absorbent article of claim 9 wherein said topsheet and said backsheet are made of a single unitary web.

11. The absorbent article of claim 6 further comprising a pair of flaps extending laterally outward from said side edges of said absorbent core.

12. The absorbent article of claim 11 wherein each said flap includes a portion of said topsheet and said backsheet.

13. The absorbent article of claim 12 wherein each said flap includes said outer portion of said topsheet.

* * * * *